(12) United States Patent
Komai et al.

(10) Patent No.: US 7,002,876 B2
(45) Date of Patent: Feb. 21, 2006

(54) ACOUSTIC-PROPAGATION-TIME MEASURING APPARATUS

(75) Inventors: Masafumi Komai, Yokohama (JP); Satoshi Nagai, Kawasaki (JP); Takehiko Suzuki, Yamato (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/896,902

(22) Filed: Jul. 23, 2004

(65) Prior Publication Data

US 2005/0018539 A1    Jan. 27, 2005

(30) Foreign Application Priority Data

Jul. 25, 2003    (JP)    ............... 2003-201992

(51) Int. Cl.
  *G01S 3/80*    (2006.01)
  *G01S 15/08*   (2006.01)
  *G01N 29/00*   (2006.01)

(52) U.S. Cl. ............... 367/99; 367/127; 73/615
(58) Field of Classification Search .......... 367/99, 367/127; 73/615
See application file for complete search history.

(56) References Cited

U.S. PATENT DOCUMENTS

| | | | | |
|---|---|---|---|---|
| 4,200,921 A | * | 4/1980 | Buckley | 367/99 |
| 5,993,393 A | | 11/1999 | Ryan et al. | |
| 6,012,332 A | * | 1/2000 | Schafer | 73/615 |
| 6,621,763 B1 | * | 9/2003 | Lyon | 367/99 |

* cited by examiner

*Primary Examiner*—Ian J. Lobo
(74) *Attorney, Agent, or Firm*—Oblon, Spivak, McClelland, Maier & Neustadt, P.C.

(57) ABSTRACT

An acoustic-propagation-time measuring apparatus includes an acoustic transmitting and receiving section having an acoustic element capable of transmitting and receiving acoustic waves, an A/D converter which converts an echo signal reflected from a target object to be measured into a digital signal, an inverse-analysis section that converts the digital echo signal into an impulse signal through inverse analysis where the digital echo signal is multiplied by an inverse matrix, a calculating section that measures an acoustic propagation time and a time difference based on the digital echo signal converted to the impulse signal, and a display section which displays the acoustic propagation time and time difference calculated by the calculating section.

11 Claims, 8 Drawing Sheets

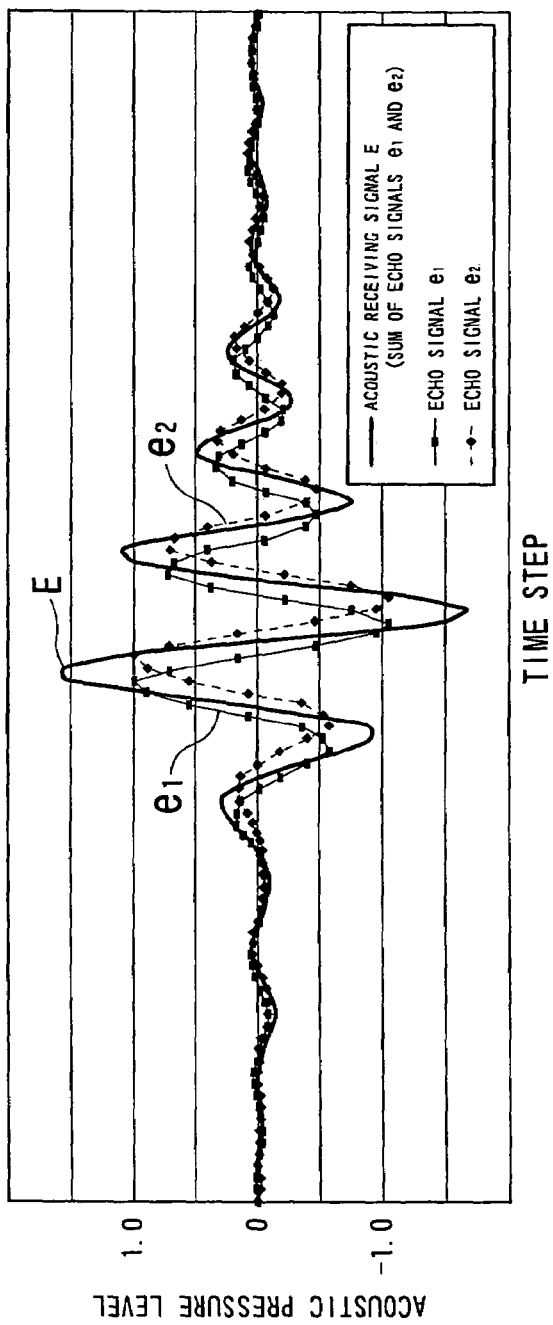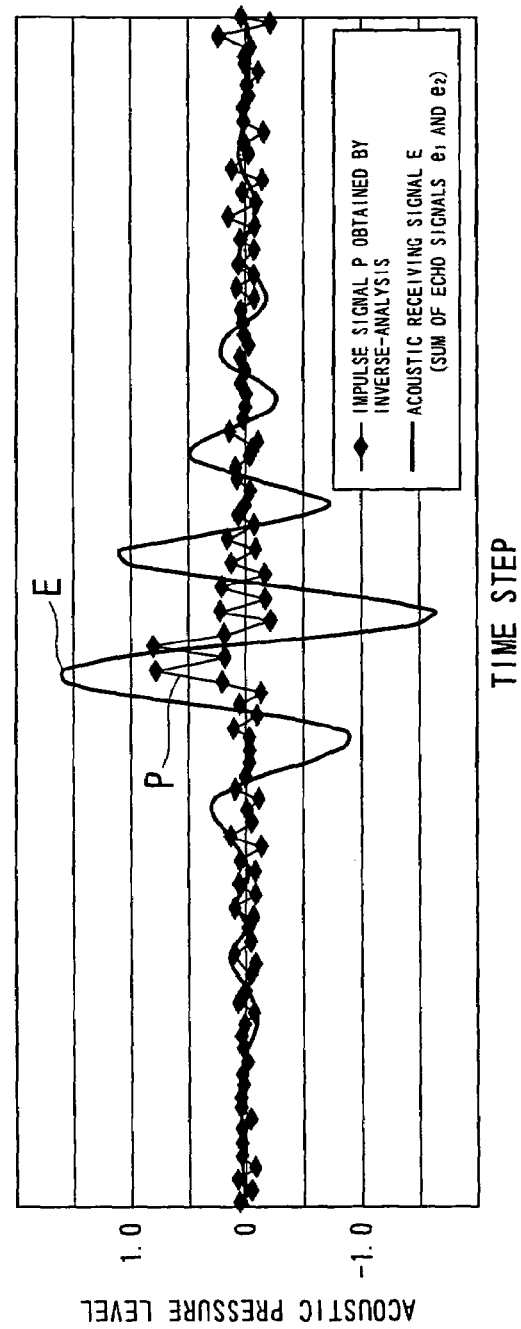
FIG. 3A
FIG. 3B

ACOUSTIC-PROPAGATION-TIME MEASURING APPARATUS

BACKGROUND OF THE INVENTION

1. Field of the Invention

The present invention relates to acoustic-propagation-time measuring apparatuses capable of performing high-accuracy analytic measurement of an acoustic propagation time in a fluid or solid. In particular, the present invention relates to an acoustic-propagation-time measuring apparatus capable of measuring the distance to an object to be measured and the distance distribution by measuring an acoustic propagation time.

2. Related Art

One conventional example of an acoustic-propagation-time measuring apparatus is a sonar device described in Japanese Patent Laid-open (KOKAI) Publication No. 2003-139855.

The sonar device described in this reference includes transmitting and receiving means having a plurality of ultrasound transducers. The sonar device emits an ultrasound signal from this transmitting and receiving means to an object and receives a reflected wave with the ultrasound transducers, realized by a plurality of receiving elements, to detect the direction and the position of the object from a phase difference and an ultrasound propagation time of the ultrasound receiving signal for display by display means.

This sonar device, used as, for example, a fish finder, is constructed so as to be capable of detecting the two-dimensional position of a reflecting object such as a school of fish. This sonar device can measure the direction and position of an object to be measured, such as a school of fish, by measuring a phase difference and an ultrasound propagation time of a signal.

Referring to FIG. 10, if a target object 1 to be measured has a bump or irregular (having protrusions and recesses) measuring surface thereon, is complicated in shape, or suffers from a complicated defect, the bump surface or shape cannot be measured correctly or the defect on the target object 1 cannot be accurately inspected with a known sonar device.

When an ultrasound is emitted from an ultrasound transducer 2 to the target object 1 disposed in a fluid and having thereon a bump or irregular portion (i.e., protruded stage or portion), two echo signals are returned, including an echo signal $e_1$ reflected from an upper surface $1a$ of the bump and an echo signal $e_2$ reflected from a lower surface $1b$ of the bump, as shown in FIG. 11A. If both echo signals $e_1$ and $e_2$ are separated from each other as shown in FIG. 11A, an acoustic propagation time $T_1$ and a time difference $t_1$ between the echo signals $e_1$ and $e_2$ can be measured correctly. Thus, the distance to the target object 1, the distance difference (gap or step), and the bump distribution can be measured with high accuracy by multiplying the measured acoustic propagation time $T_1$ and the time difference $t_1$ by the acoustic velocity.

Referring to FIG. 11B, however, if the target object 1 to be measured has only a small bump or if both the echo signals $e_1$ and $e_2$ overlap by being only slightly shifted, i.e., the ultrasound waveform components overlap each other, an acoustic propagation time difference $t_2$ cannot be extracted correctly for accurate measurement, and consequently, the distance, distance difference (gap), bump distribution, or shape in relation to the target object 1 cannot be measured with high accuracy.

SUMMARY OF THE INVENTION

In view of the circumstances encountered in the prior art mentioned above, an object of the present invention is to provide an acoustic-propagation-time measuring apparatus capable of correctly performing high-accuracy analytic measurement of an acoustic propagation time by converting a reflected acoustic signal to an impulse signal.

Another object of the present invention is to provide an acoustic-propagation-time measuring apparatus capable of correctly measuring an acoustic propagation time to measure, with high accuracy, the distance, distance difference, bump or irregularity distribution, and shape in relation to a target object in a fluid or solid.

The above and other objects can be achieved according to the present invention by providing an acoustic-propagation-time measuring apparatus which comprises:

an acoustic receiving device having at least one acoustic element capable of receiving a transmitted acoustic wave;

an A/D converter for converting an acoustic receiving signal to a digital echo signal, the acoustic receiving signal being reflected from a target object to be measured and received by the acoustic element of the acoustic receiving device;

an inverse-analysis device for carrying out inverse-analysis processing of multiplying the digital echo signal by an inverse matrix to convert the digital echo signal into an impulse signal;

a calculating device for calculating an acoustic propagation time and a time difference of the acoustic receiving signal in response to the impulse signal produced by the inverse-analysis device; and a display device for displaying the acoustic propagation time and the time difference calculated by the calculating device.

In a preferred embodiment of the present invention of the aspect mentioned above, it is preferred that the inverse-analysis device samples an acoustic receiving signal including an acoustic signal from the acoustic element, a characteristic of a propagation field of the acoustic signal, and a receiving characteristic of the acoustic element into vertical elements of a matrix to convert the acoustic receiving signal into time-series data in steps, produces an inverse matrix from the matrix of the time series data, and multiplies the acoustic receiving signal by the inverse matrix to convert the acoustic receiving signal into the impulse signal.

It is also preferred that the inverse-analysis device adds white noise with a value being small enough compared with the acoustic receiving signal to vertical elements of a matrix containing time-series data of the acoustic receiving signal to calculate an inverse matrix, carries out the inverse-analysis processing of multiplying the acoustic receiving signal by the inverse matrix two or more times to average the results of the inverse analysis processing to calculate the mean value, and sets the mean value as the impulse signal of the acoustic receiving signal, and the calculating device calculates the acoustic propagation time and the time difference of the acoustic receiving signal.

The acoustic-propagation-time measuring apparatus may further comprise a digital data-recording unit between the A/D converter and the inverse-analysis device, the digital-data recording unit temporarily storing the digital echo signal generated by the A/D converter.

The acoustic receiving device may include a plurality of at least one of the acoustic elements, in which an emitting and receiving unit applies an impulse voltage to the plurality of acoustic elements.

The calculating device may be provided with a propagation-time-and-distance calculating function for multiplying the calculated acoustic propagation time and the time difference by an acoustic velocity to measure the distance from the acoustic element to the target object, a distance difference, and bump distribution.

The display device may be provided with a propagation-time-and-distance display function for displaying the acoustic propagation time, the time difference, the distance from the acoustic element to the target object, a distance difference, and bump distribution calculated by the calculating device.

The acoustic-propagation-time measuring apparatus may further comprise a noise filter for eliminating noise adjacent to a digital echo signal input end of the inverse-analysis device.

It may be further preferred that the inverse-analysis device includes inverse-analysis correcting unit for correcting an inverse-analysis result, in which the inverse-analysis correcting unit optimizes vertical elements of a matrix for the inverse-analysis processing in response to an acoustic receiving signal from a reference target object for measuring a reference acoustic propagation time.

The inverse-analysis device may include a communication unit connected to another remote inverse-analysis device, in which the remote inverse-analysis device receives signal data of the acoustic receiving signal from the communication unit to share the time-consuming inverse-analysis processing, transmits a result of the inverse-analysis processing to the calculating device, and the display device displays the result.

Moreover, the calculating device may also include an aperture-synthesizing unit for carrying out calculation of imaging a measurement surface of the target object by aperture synthesis, the measurement surface being subjected to three-dimensional measurement.

In the acoustic-propagation-time measuring apparatuses according to the present invention of the structures and characters mentioned above, a reflected acoustic signal (digital echo signal) from the target object is subjected to the inverse analysis by the inverse-analysis device to convert the reflected acoustic signal to an impulse signal. Using this impulse signal, the acoustic propagation time and the time difference can be calculated or measured with high accuracy.

Furthermore, the acoustic-propagation-time measuring apparatuses according to the present invention are capable of measuring an acoustic propagation time and a time difference with high accuracy, so that the distance from the acoustic element to the target object and a distance difference (gap) and bump distribution on the target object can be measured with accuracy on the order of millimeters or less. Accordingly, it becomes possible to correctly measure a defect on the target object and the degree of the defect, and to detect the location and shape of the target object.

The nature and further characteristic features of the present invention will be made more clear from the following descriptions made with reference to the accompanying drawings.

BRIEF DESCRIPTION OF THE DRAWINGS

In the accompanying drawings:

FIG. 3A shows an acoustic receiving signal (digital echo signal) including echo signals from the upper surface and the lower surface of a bump on an target object, as measured by an acoustic-propagation-time measuring apparatus according to the present invention, and FIG. 3B shows an impulse signal produced by applying inverse-analysis to the acoustic receiving signal shown in FIG. 3A;

DESCRIPTION OF THE PREFERRED EMBODIMENTS

Preferred embodiments of an acoustic-propagation-time measuring apparatus according to the present invention will be described hereunder with reference to the accompanying drawings.

Figure 1:
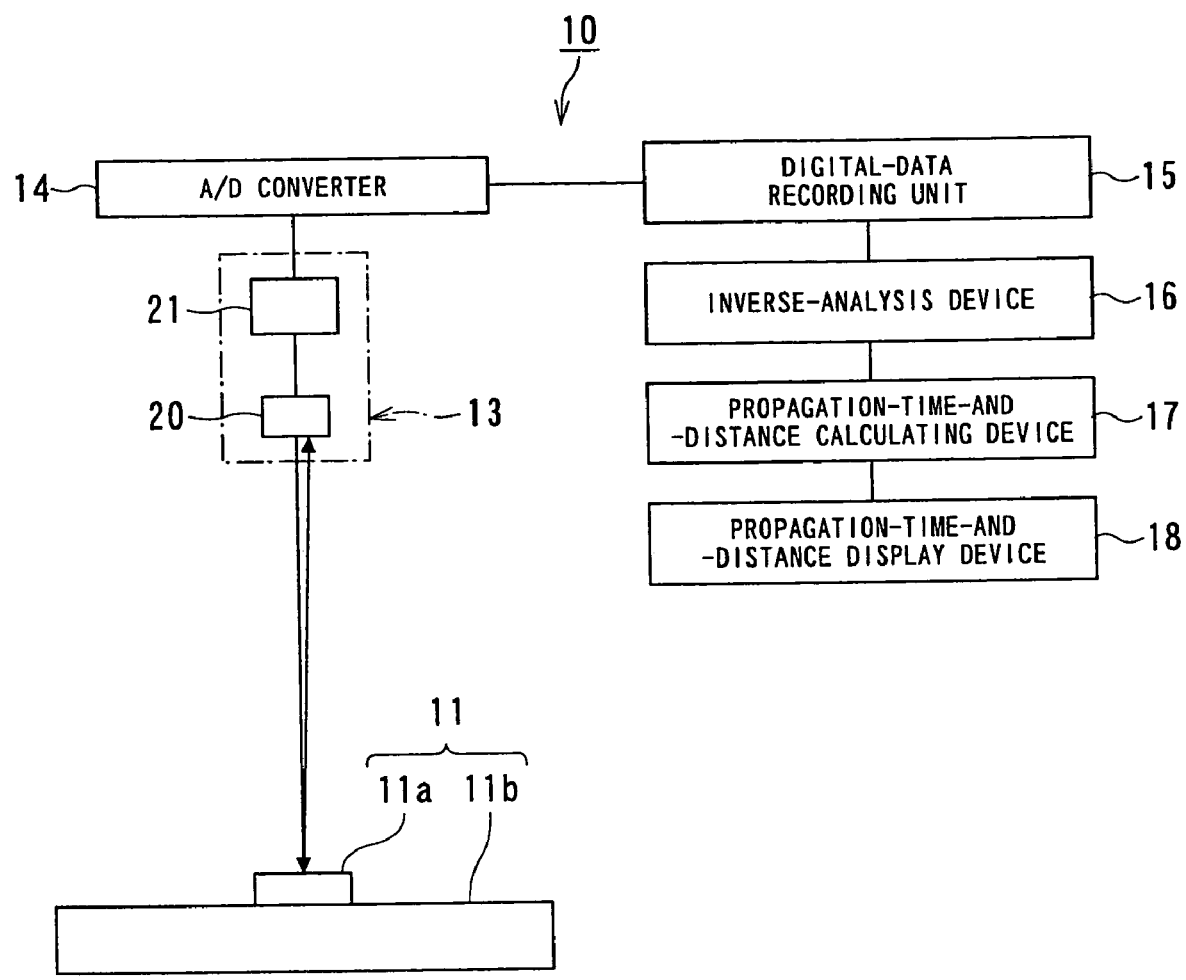
FIG. 1 is an outline block diagram showing an acoustic-propagation-time measuring apparatus according to a first embodiment of the present invention.

FIG. 1 shows an embodiment where an acoustic-propagation-time measuring apparatus according to the present invention is applied to an acoustic-based distance-measuring apparatus 10.

This distance-measuring apparatus 10 measures an acoustic propagation time and a time difference, and from this acoustic propagation time, correctly calculates the distance, distance difference (gap or step), and bump or irregularity distribution in relation to a target object 11 to be measured, and detects the position and shape of the target object 11. Further, it is to be noted that the term "bump" or "irregularity" used herein may mean a protruded/recessed surface condition.

The distance-measuring apparatus 10 can correctly measure the position and shape of the target object 11 in water, oil, or fluid of metallic sodium or the target object 11 in a solid of, for example, a metallic material or concrete. If the target object 11 suffers from a defect or deformation, the distance-measuring apparatus 10 can even detect such a defect and the degree of deformation of the target object 11.

Referring to FIG. 1, the distance-measuring apparatus 10 includes: a transmitting and receiving device 13 that transmits and/or receives highly directional acoustic waves such as ultrasound; an A/D converter 14 that converts an echo signal received by this transmitting and receiving device 13 to a digital signal; a digital-data recording device 15 that temporarily records, as digital data, a digital echo signal from the A/D converter 14; an inverse-analysis device 16 that converts the above-described digital echo signal to an impulse signal through inverse analysis; a propagation-time-and-distance calculating device 17, as arithmetic-operation means, that measures an acoustic propagation time and time difference by analyzing the digital echo signal converted to an impulse signal and carries out arithmetic operations for the distance, distance difference (gap), and bump distribution in relation to the target object 11 by multiplying the obtained acoustic propagation time and time difference by the acoustic velocity; and propagation-time-and-distance display device 18 that displays the acoustic propagation time and time difference for which arithmetic operations have been carried out by this acoustic propagation-time-and-distance calculating device 17, as well as the distance, the distance difference (gap), and the bump distribution in relation to the target object 11.

The transmitting and receiving device 13 of the distance-measuring apparatus 10 includes a single acoustic element 20 and an emitting and receiving unit 21 that applies an impulse voltage to this acoustic element 20. The emitting and receiving unit 21 receives an impulse from a controlling element, not shown, and applies the impulse voltage to the acoustic element 20, which then emits highly directional acoustic waves such as ultrasound. Although, in this embodiment, the transmitting and receiving device 13 is provided with a function for carrying out both the transmission and reception of acoustic waves, a transmitting device and a receiving device may be provided separately so as to carry out transmission and reception functions independently.

The acoustic element 20 is realized by, for example, a piezoelectric element that excites an elastic waveform in a piezoelectric material with an applied voltage to generate ultrasound of about 0.8 to 200 MHz resulting from a piezoelectric effect due to a resonance phenomenon, a magnetostrictive element that generates acoustic waves with a frequency of about several kilohertz to 100 kHz based on a magnetostrictive phenomenon of a magnetic material, or an electrostrictive element based on an electrostrictive phenomenon. The acoustic element 20 functions as an inter-transducer for bi-directional conversion between an acoustic vibration and an electrical signal. The acoustic element 20 is typically an electromagnetic or piezoelectric ultrasound transducer.

When an impulse voltage is applied to the acoustic element 20 from the emitting and receiving unit 21 of the transmitting and receiving device 13, the acoustic element 20 outputs a composite signal including a signal with the natural vibration component thereof and an exponentially attenuating signal superimposed thereon. The acoustic wave, i.e., the composite signal, is emitted towards the target object 11 disposed in a fluid such as air, water, oil, or metallic sodium and is then reflected from the target object 11.

The acoustic wave reflected from the target object 11 is again received by the acoustic element 20, which then transmits the acoustic wave, as an acoustic echo signal (acoustic receiving signal), to the acoustic signal emitting and receiving unit 21, where the acoustic echo signal is amplified and converted to an electrical echo signal. This electrical echo signal is converted to a digital echo signal by the A/D converter 14. The digital echo signal is once stored in the digital-data recording unit 15 as digital data.

Figure 2A:
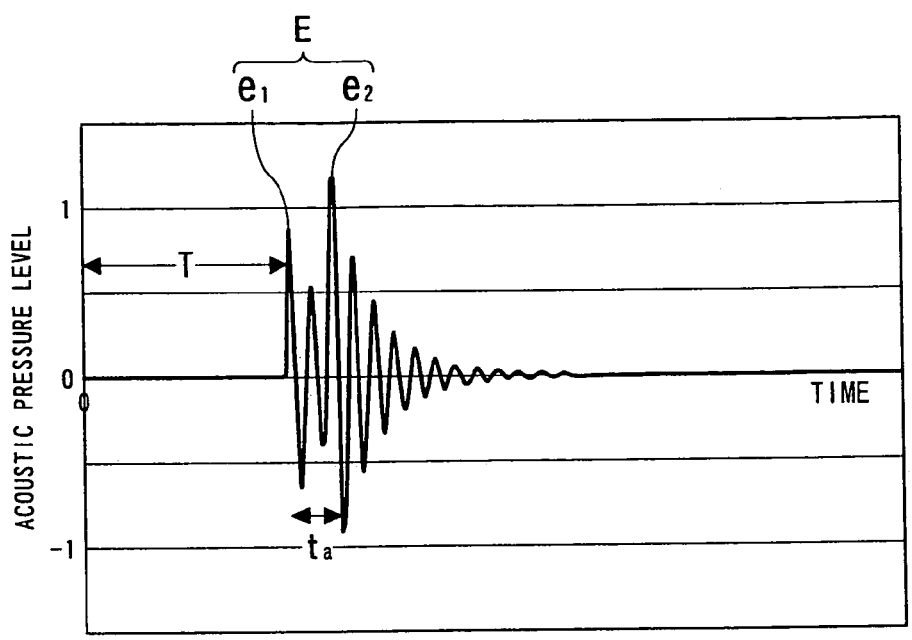
FIG. 2A shows an acoustic receiving signal (digital echo signal) as measured by an acoustic-propagation-time measuring apparatus according to the present invention.
Figure 2B:
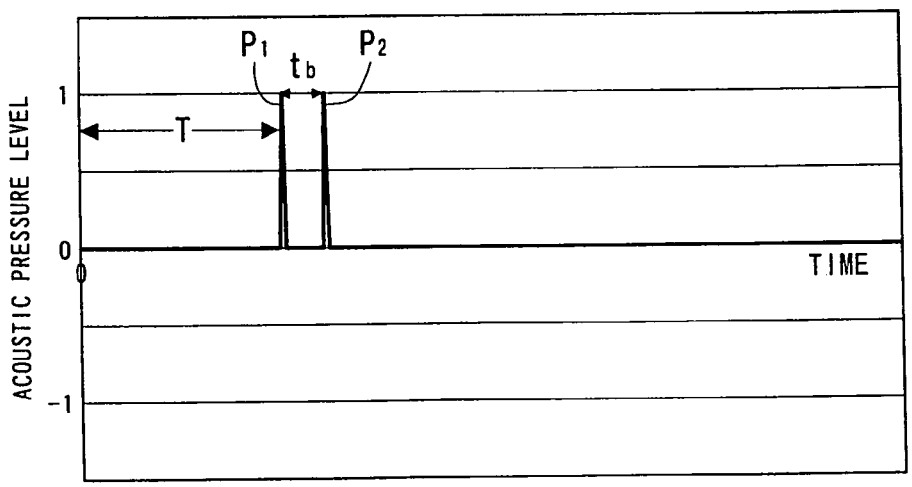
FIG. 2B shows an impulse signal produced by applying inverse-analysis to the acoustic receiving signal (digital echo signal) shown in FIG. 2A.

Referring to FIGS. 2A and 2B, the digital echo signal (denoted as E in FIG. 2A) returns to the acoustic element 20 a certain acoustic propagation time T after the acoustic wave has been emitted from the acoustic element 20. The digital echo signal E includes an echo signal $e_1$ reflected from an upper surface 11a of the bump (or step) on the target object 11 and an echo signal $e_2$ reflected from a lower surface 11b of the bump (or step), as shown in FIG. 1. With a known distance-measuring apparatus, it is difficult to measure a difference in acoustic propagation time between the acoustic wavelengths of the echo signals $e_1$ and $e_2$, i.e., a difference $t_a$ in acoustic propagation time in the gap portion, if the acoustic wavelengths of the echo signals $e_1$ and $e_2$ overlap each other, as shown in FIG. 2A.

In the acoustic-based distance-measuring apparatus 10 shown in FIG. 1, however, the inverse-analysis device 16 applies inverse analysis to the digital echo signal E to convert the signal E into impulses, i.e., to sharpen the signal E, so that the echo signals $e_1$ and $e_2$ appear separated from each other, as shown by impulse signals $P_1$ and $P_2$ in FIG. 2B. The impulse signals $P_1$ and $P_2$ generated through inverse-analysis correspond to the upper surface 11a and the lower surface 11b of the bump on the target object 11, respectively. The impulse signals $P_1$ and $P_2$ thus generated are clearly separated from each other, unlike the echo signals $e_1$ and $e_2$, which advantageously enables an acoustic propagation time $t_b$ between the impulse signals $P_1$ and $P_2$ to be measured with high accuracy.

With the acoustic-based distance-measuring apparatus 10 shown in FIG. 1, even if the target object 11 has a small bump or irregularity, i.e., a bump or irregularity with a short gap, the acoustic propagation time difference $t_b$ associated with the gap portion can be measured correctly as a result of the inverse-analysis device 16 carrying out inverse analysis. With the acoustic-based distance-measuring apparatus 10, a gap can be measured with an accuracy of at least millimeter order, depending on the oscillation frequency (wavelength λ) and the acoustic velocity of the acoustic wave. More specifically, a gap size of about 0.3 mm to 0.4 mm can be measured with high accuracy if the gap is measured in water using ultrasound. If the gap is measured in metallic sodium, a resolution of about 0.5 mm is achieved. Furthermore, if the gap is measured in air, a resolution of about 1.5 mm to 2.0 mm is achieved, so that the shape of the target 11 to be measured can be identified and the presence of a defect in the target object 11 can be inspected with high accuracy.

As described above, the inverse-analysis device 16 applies the inverse analysis to the digital echo signal E to convert the signal E into the impulse signals $P_1$ and $P_2$, as shown in FIG. 2B. In response to the impulse signals $P_1$ and $P_2$, the calculating device 17 calculates the acoustic propagation time T and the acoustic propagation time difference $t_b$. The acoustic propagation time T and the difference $t_b$ are further multiplied by the acoustic velocity to produce the distance and distance difference, respectively, to the target object 11. As described above, the calculating device 17 has a function for calculating the acoustic propagation time T and the time difference $t_b$, and furthermore, for calculating the distance to the target object 11, the distance difference (gap), and the bump distribution. The distance and the distance difference calculated by the calculating device 17 are displayed on the display device 18. Thus, the distance from the acoustic element 20 to the target object 11 to be measured, and if there is a bump or irregularity on the target object 11, the distance difference (gap) can be measured with high accuracy based on the acoustic propagation time difference $t_b$, which is clearly identifiable through the inverse analysis.

The inverse analysis by the inverse-analysis device 16 will be described hereunder.

In the inverse-analysis device 16, the inverse analysis of the digital echo signal E is carried out by calculating an n-order square matrix A.

The n-order square matrix A is represented by the following Expression (1) using array entries $a_{kl}$.

[Expression 1] (1)

$$A = \begin{bmatrix} a_{11} & a_{12} & \cdots & a_{1l} & \cdots & a_{1n} \\ a_{21} & a_{22} & \cdots & a_{2l} & \cdots & a_{2n} \\ \vdots & \vdots & & \vdots & & \vdots \\ a_{k1} & a_{k2} & \cdots & a_{kl} & \cdots & a_{kn} \\ \vdots & \vdots & & \vdots & & \vdots \\ a_{n1} & a_{n2} & \cdots & a_{nl} & \cdots & a_{nn} \end{bmatrix}$$

A relationship as shown by the following Expression (2) is established between the observed time-series signal (corresponding to the time-series data of the digital echo signal E), denoted as a column vector (column matrix) yi, and the target impulse response time series, denoted as a column vector (column matrix) xi, using Y (vector) representing the column vector yi and using X (vector) representing the column vector xi.

[Expression 2]

$Y = (y_1\ y_2\ y_3 \ldots y_{n-1}\ y_n)^T$ $X = (x_1\ x_2\ x_3 \ldots x_{n-1}\ x_n)^T$ $Y = AX$ (2)

where T represents a transposed matrix.

From the Expression (2), X is obtained using the inverse matrix $A^{-1}$ of the n-order square matrix A, as shown by the following Expression (3).

[Expression 3]

$X = A^{-1} Y$ (3)

The waveform data of an acoustic receiving signal measured by the acoustic-based distance-measuring apparatus 10 is indicated in time series by the solid line E in FIG. 3A. This waveform data E, i.e., the digital echo signal E is equivalent to the sum of the echo signal $e_1$, corresponding to the upper surface 11a of the bump, and the echo signal $e_2$, corresponding to the lower surface 11b of the bump on the target object 11.

Data series Pi is expressed by the following Expression (4) using the waveform data (digital echo signal) E of an actually measured acoustic receiving signal, denoted as u.

[Expression 4] (4)

$$Pi = \begin{cases} i < 0 & \rightarrow Pi = 0 \\ 0 \leq i \leq L & \rightarrow Pi = u_i \\ L < i & \rightarrow Pi = 0 \end{cases}$$

where L indicates a location on the time-step axis at which the amplitude of the acoustic receiving signal (digital echo signal) E is attenuated enough to cause the acoustic pressure level to be close to zero.

If the symbol "i" in the Expression (4) which gives the maximum value of the data series Pi is denoted as $i_{max}$, an array element $a_{kl}$ which is the entry in the k-th row of the l-th column in the n-order square matrix A in the Expression (1) is represented by the following Expression (5) using the data series Pi and $i_{max}$.

[Expression 5] (5)

$$a_{kl} = \begin{cases} k < l - i\max & \rightarrow a_{kl} = 0 \\ l - i\max \leq k \leq l - \max + L & \rightarrow a_{kl} = P_{k-l+i\max} \\ l - i\max + L < k & \rightarrow a_{kl} = 0 \end{cases}$$

In the Expression (5), the matrix A is set so as to have diagonal components having large absolute values, i.e., such that the maximum acoustic pressure value of the acoustic receiving signal (digital echo signal) E is set as the diagonal components in the matrix A by arranging the time-series data of the acoustic receiving signal (digital echo signal) E sequentially in the columns.

The matrix A, in which the array entry $a_{kl}$ in the k-th row of the l-th column is represented by the Expression (5), can have diagonal components having large absolute values, and hence, the digital echo signal (acoustic receiving signal) E can be converted to an impulse signal for sharpening through the inverse analysis where the column vector Y of the observed time-series signal yi, i.e., the acoustic receiving signal E is multiplied by the inverse matrix $A^{-1}$ of the matrix A.

An impulse signal P, i.e., an impulse response, is obtained by applying the inverse analysis to the digital echo signal E as shown in FIG. 3A.

When the array entry $a_{kl}$ in the k-th row of the l-th column is set as represented by the Expression (5), the matrix A can have diagonal components having large absolute values, which enables a stable inverse matrix $A^{-1}$ to be calculated. As shown in FIGS. 3A and 3B, a sharpened signal, i.e., an impulse signal P can be produced using the inverse matrix $A^{-1}$ from the signal series of the acoustic receiving signal E, which is the sum of the echo signals $e_1$ and $e_2$. This enables the echo signals $e_1$ and $e_2$, even if they are extremely close to each other, to be distinguished from each other for measurement.

In the distance-measuring apparatus 10 using acoustic wave, the inverse-analysis device 16 arranges the time-series data of the acoustic receiving signal (digital echo signal) E as vertical (column) components of the matrix A by dividing the presumed acoustic propagation time into time steps each equivalent to the acoustic propagation time difference, i.e., the sampling time step for A/D conversion. Thereafter, the inverse matrix $A^{-1}$ is obtained from the matrix A composed of the thus arranged time-series data, and the acoustic receiving signal E is then multiplied by the thus obtained inverse matrix $A^{-1}$. An impulse signal is thus reproducible from the acoustic receiving signal E. Thus, the acoustic propagation time and the time difference can be measured with high accuracy by analyzing this impulse signal.

In this case, the inverse-analysis device 16 can carry out two or more inverse analysis operations in each of which white noise having a value small enough compared with the time-series data of the acoustic receiving signal E is added to the acoustic receiving signal E, and then the result is multiplied by the inverse matrix $A^{-1}$. The two or more results thus obtained are averaged to calculate the mean value, which is set as an impulse signal. This operation enables more stable impulse response characteristics to be achieved.

White noise σ having a value being small enough compared with the time-series data of the acoustic receiving signal E is added to each of the matrix elements $a_{kl}$ of the matrix A, as shown in the following Expression (6), and the result is then multiplied by the inverse matrix $A^{-1}$. This sequence of processing is repeated two or more times. A plurality of such impulse response results are added together to calculate the mean value. This enables a more stable inverse-analysis result to be produced from the acoustic receiving signal E.

[Expression 6] (6)

$$a_{kl} = \begin{cases} k < l - i\max & \rightarrow a_{kl} = \sigma \\ l - i\max \leq k \leq l - i\max + L & \rightarrow a_{kl} = P_{k-l+i\max} \\ l - i\max + L < k & \rightarrow a_{kl} = \sigma \end{cases}$$

Figure 4:
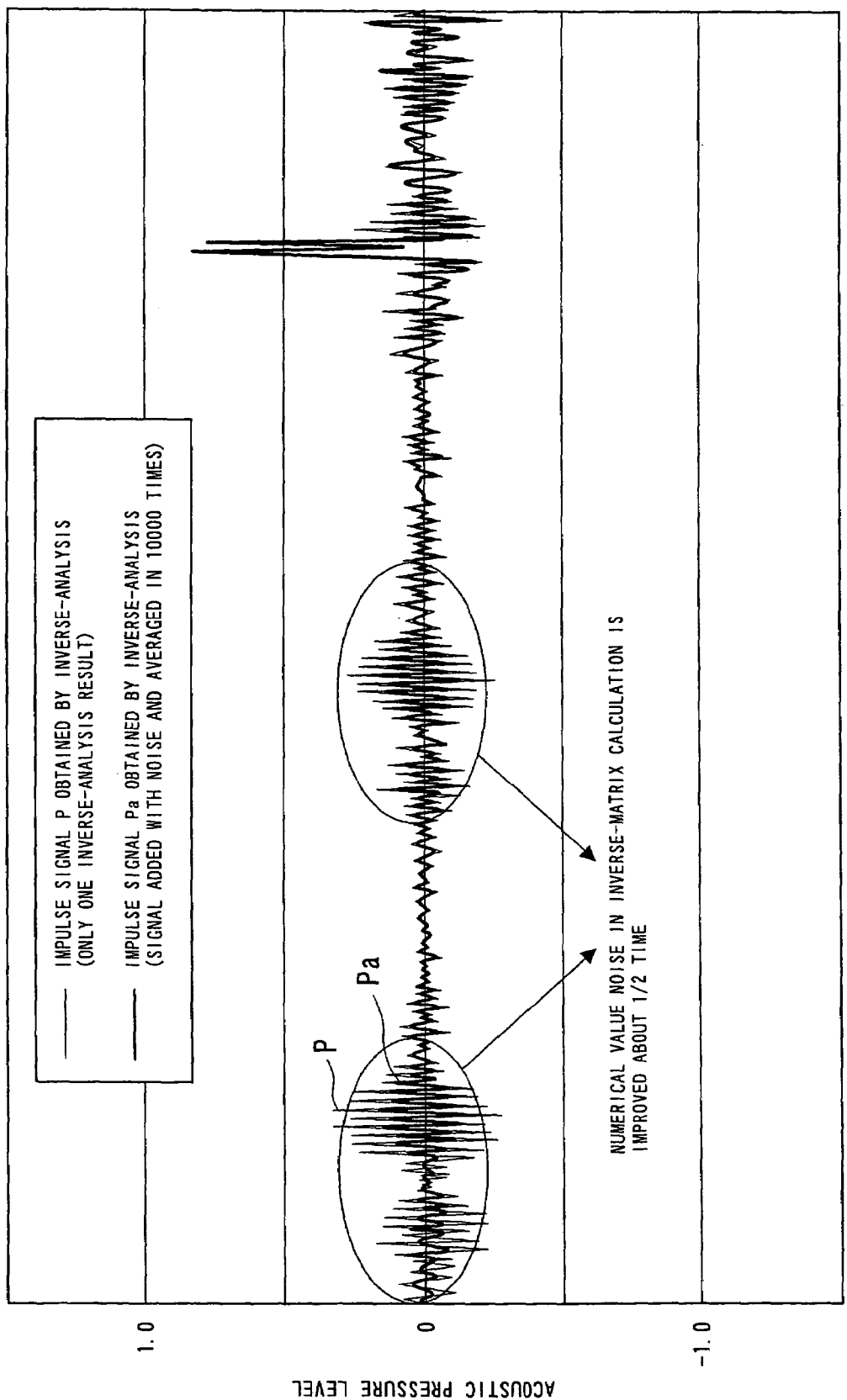
FIG. 4 shows a result of averaging two or more inverse analysis operations by inverse-analysis means of an acoustic-propagation-time measuring apparatus according to the present invention, where white noise is added to the time-series data of an acoustic receiving signal.

FIG. 4 shows an example of a result of the inverse analysis in which the white noise is added to the matrix elements in the acoustic-based distance-measuring apparatus 10.

Random noise (white noise) with a maximum value being small enough (one-hundredth, for example) compared with the maximum value in the vertical (column) array elements Pi of the matrix A is added, and an impulse response is calculated by multiplying by the inverse matrix $A^{-1}$. FIG. 4 shows the mean value of the results obtained through 10000 calculations for an impulse signal. This averaging of the results of the repeated calculations can reduce the numeric computational noise by a factor of about two.

In FIG. 4, the thin line P indicates an impulse signal obtained through one inverse analysis operation, whereas the thick line Pa indicates an impulse signal obtained by carrying out 10000 times of inverse analysis operations and then averaging the results.

Figure 5:
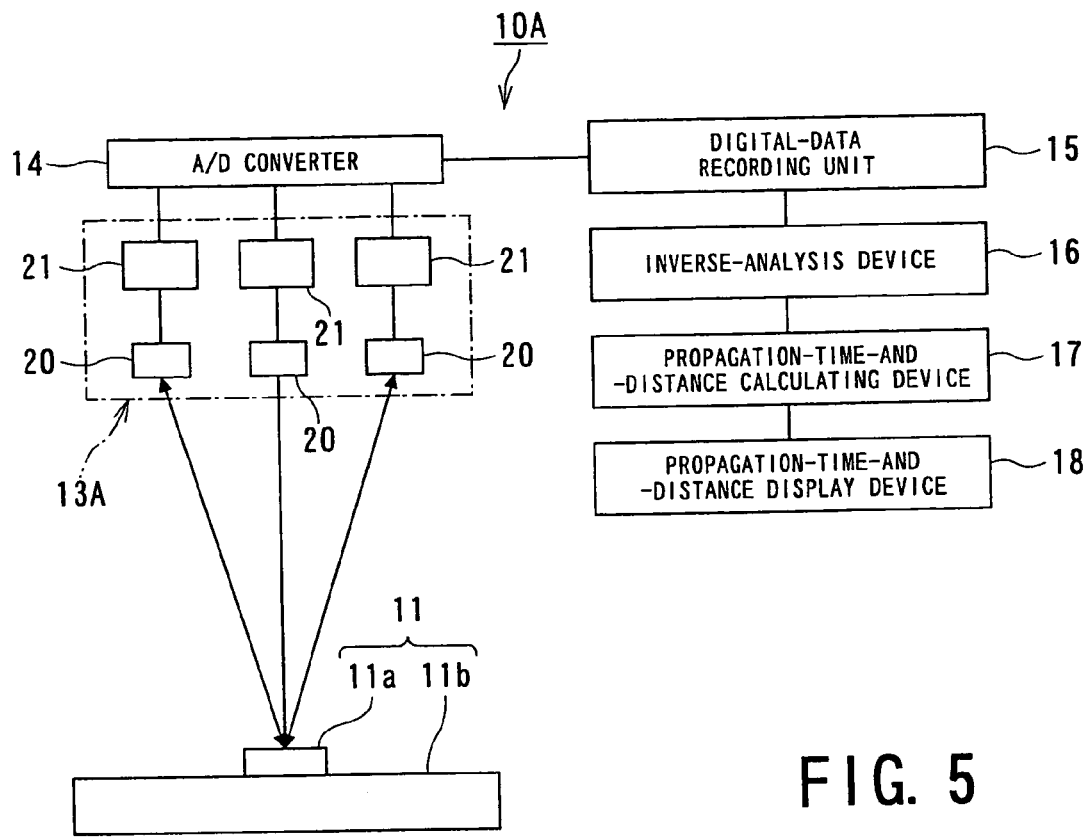
FIG. 5 is an outline block diagram showing an acoustic-propagation-time measuring apparatus according to a second embodiment of the present invention.

FIG. 5 is an outline block diagram showing an acoustic-propagation-time measuring apparatus according to the second embodiment of the present invention.

An acoustic-propagation-time measuring apparatus 10A of this second embodiment basically has the same structure as that of the acoustic-propagation-time measuring apparatus (distance-measuring apparatus) 10 of the first embodiment shown in FIG. 1, except that the acoustic-propagation-time measuring apparatus 10A is provided with a transmitting and receiving device 13A. The same components as those of the acoustic-propagation-time measuring apparatus 10 are denoted by the same reference numerals and will not be described here.

This acoustic-propagation-time measuring apparatus 10A is applied to a distance-measuring apparatus utilizing acoustic wave, and the transmitting and receiving device 13A includes a plurality pairs of the acoustic element 20 and the emitting and receiving unit 21. An impulse voltage may be applied to the plurality of acoustic elements 20 from one of the emitting and receiving units 21, and an acoustic echo signal received by each of the acoustic elements 20 is sent to the A/D converter 14 via the emitting and receiving unit 21.

In this acoustic-propagation-time measuring apparatus 10A, the acoustic echo signal reflected from the target object 11 is again received by the acoustic elements 20, and the received acoustic echo signal is amplified in the emitting and receiving unit 21 and is then converted into an electrical echo signal so as to generate a digital echo signal (acoustic receiving signal). The inverse-analysis device 16 then multiplies this digital echo signal by the inverse matrix $A^{-1}$ to convert the digital echo signal into an impulse signal. According to this reason, the distances and distance differences (gaps) can be measured in a wide range at the same time, and an acoustic propagation time and a time difference can be also measured with high accuracy. The distance from an acoustic element 20 to the target object 11 to be measured and the bump distribution can be measured by multiplying the acoustic propagation time and the time difference measured in this measuring apparatus 10A by the acoustic velocity, and therefore, the bumps or irregularities in a wider range on the target object 11 can be measured at the same time.

Figure 6:
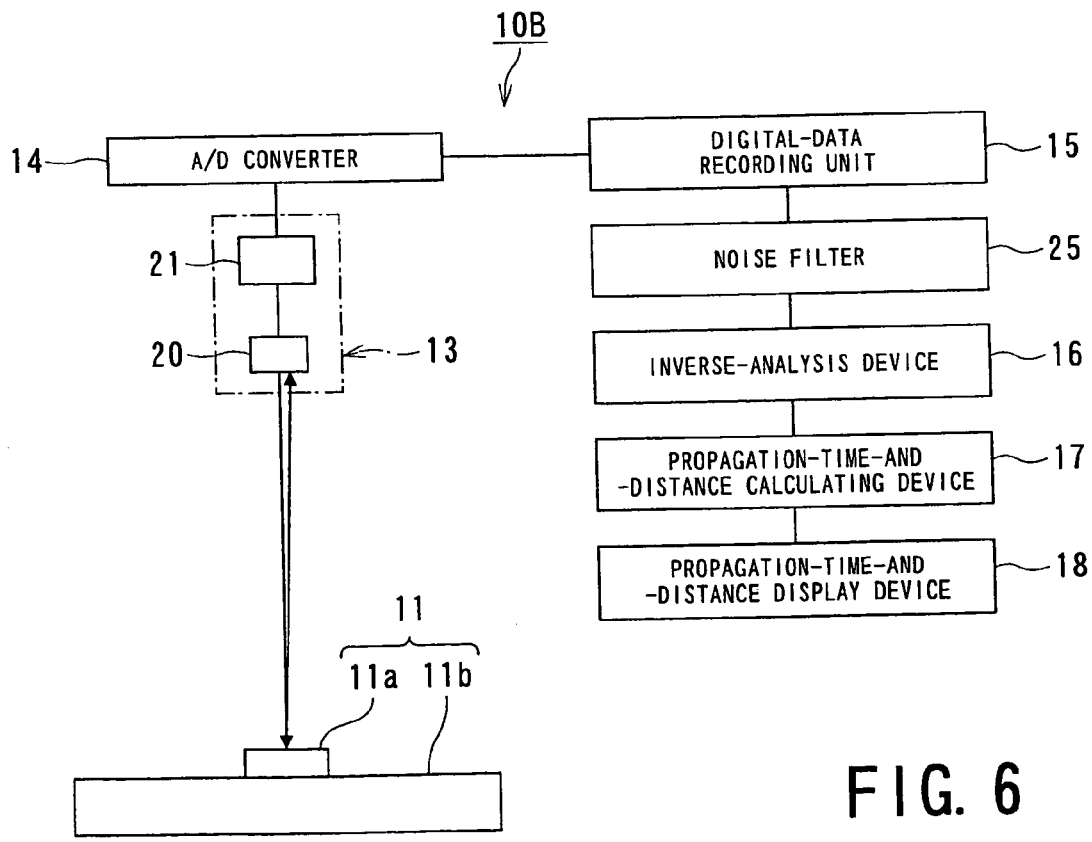
FIG. 6 is an outline block diagram showing an acoustic-propagation-time measuring apparatus according to a third embodiment of the present invention.

FIG. 6 is an outline block diagram showing an acoustic-propagation-time measuring apparatus according to the third embodiment of the present invention.

An acoustic-propagation-time measuring apparatus 10B according to this third embodiment has basically the same structure as that of the first embodiment shown in FIG. 1, except that the measuring apparatus 10B additionally includes a noise filter 25. The same components as those of the acoustic-propagation-time measuring apparatus 10 are denoted by the same reference numerals and will not be described.

The noise filter 25 is provided between the digital-data recording unit 15 and the inverse-analysis device 16. With this noise filter 25, noise is eliminated from the digital echo signal E, i.e., an acoustic receiving signal at the signal input end of the inverse-analysis device 16. After the acoustic-propagation-time measuring apparatus 10B is thus made resistive to noise, calculation errors during the inverse analysis can be reduced. Furthermore, with the noise filter 25, the noise component contained in the digital echo signal E is eliminated to reduce the calculation errors during the inverse analysis. Thus, an acoustic propagation time and a time difference can be measured more stably with high accuracy.

Figure 7:
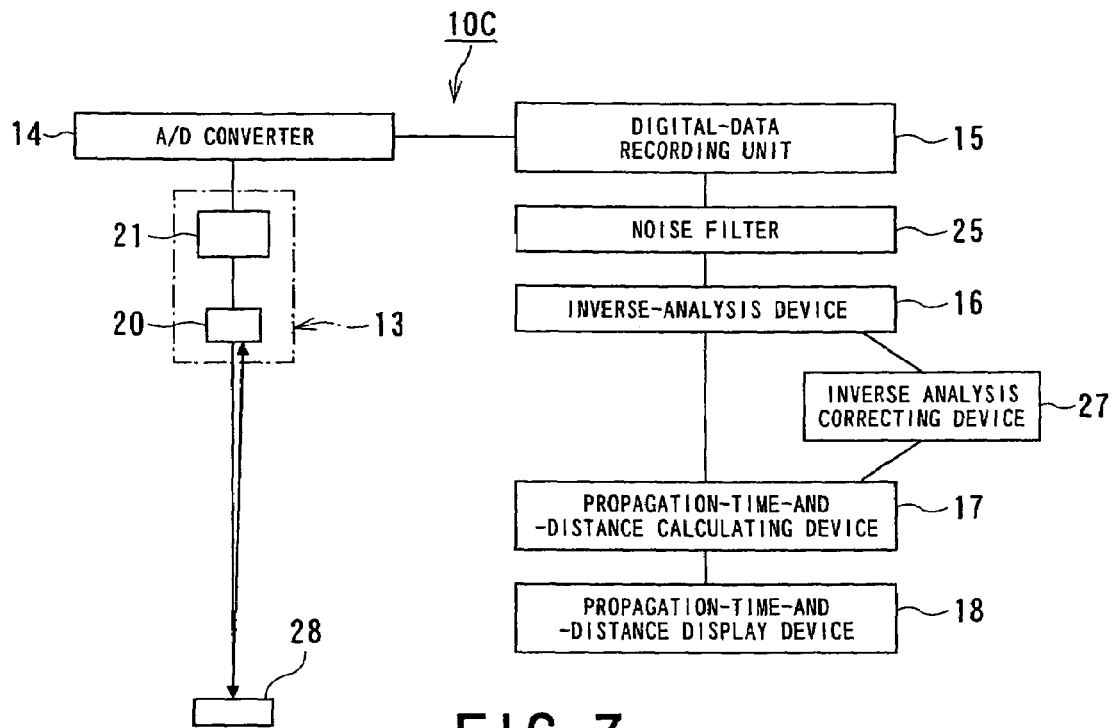
FIG. 7 is an outline block diagram showing an acoustic-propagation-time measuring apparatus according to a fourth embodiment of the present invention.

FIG. 7 shows an acoustic-propagation-time measuring apparatus according to the fourth embodiment of the present invention.

An acoustic-propagation-time measuring apparatus 10C according to this fourth embodiment has basically the same structure as that of the third embodiment shown in FIG. 6, except that the measuring apparatus 10C additionally includes an inverse-analysis correcting device 27. The same components as those of the acoustic-propagation-time measuring apparatus 10B shown in FIG. 6 are denoted by the same reference numerals and will not be described.

The acoustic-propagation-time measuring apparatus 10C shown in FIG. 7 additionally includes the noise filter 25 and the inverse-analysis correcting device 27, compared with the acoustic-propagation-time measuring apparatus 10 of the first embodiment shown in FIG. 1. The noise filter 25 is provided between the digital-data recording unit 15 and the inverse-analysis device 16, and the inverse-analysis correcting device 27 is provided between the inverse-analysis device 16 and the propagation-time-and-distance calculating device 17.

The inverse-analysis correcting device 27 uses a reference object 28 functioning as a standard for calibration to optimize the vertical components of the inverse-analysis matrix by the inverse-analysis device 16.

This acoustic-propagation-time measuring apparatus 10C includes the inverse-analysis correcting device 27, which uses an acoustic echo signal reflected from the reference object 28 to optimize inverse analysis by the inverse-analysis device 16. This inverse-analysis correcting device 27 inputs, as a reflected acoustic signal (digital echo signal), a change in acoustic waveform resulting from characteristic changes or characteristic deterioration in the acoustic element 20 or characteristic changes in the acoustic propagation field (air, fluid or solid field) by using the reference object 28 to correct the change in the acoustic waveform. Thus, the inverse analysis by the inverse-analysis device 16 can be performed reliably with much higher accuracy for the high-accuracy calculation of the impulse response.

This acoustic-propagation-time measuring apparatus 10C provided with the inverse-analysis correcting device 27 optimizes the matrix elements for the inverse analysis by the inverse-analysis device 16 after receiving an acoustic echo signal reflected from the reference object 28 as an acoustic receiving signal. This inverse-analysis correcting device 27 can flexibly adjust to changes in the time-series signal of the acoustic wave signal resulting from characteristic changes in the acoustic element 20 or characteristic changes in the acoustic propagation field, thus calibrating the inverse-analysis device 16 so as to always ensure the optimal inverse analysis.

With the inverse-analysis correcting device 27, the inverse-analysis device 16 is calibrated in response to an acoustic signal (digital echo signal E) reflected from the reference object 28 so as to produce an optimal result of the inverse analysis. This enables the inverse-analysis device 16 to convert a reflected acoustic signal to an impulse signal through the optimal inverse analysis. A high-accuracy impulse response is achieved by the optimized inverse-analysis device 16 for converting a reflected acoustic signal (digital echo signal) to an impulse signal for the measurement of the target object 11. This enables an acoustic propagation time and a time difference to be measured with high accuracy at all times. The distance from the acoustic element 20 to the target object 11 and the distance difference (gap) can be measured with high accuracy by multiplying the measured acoustic measurement time and the time difference by the acoustic velocity.

Figure 8:
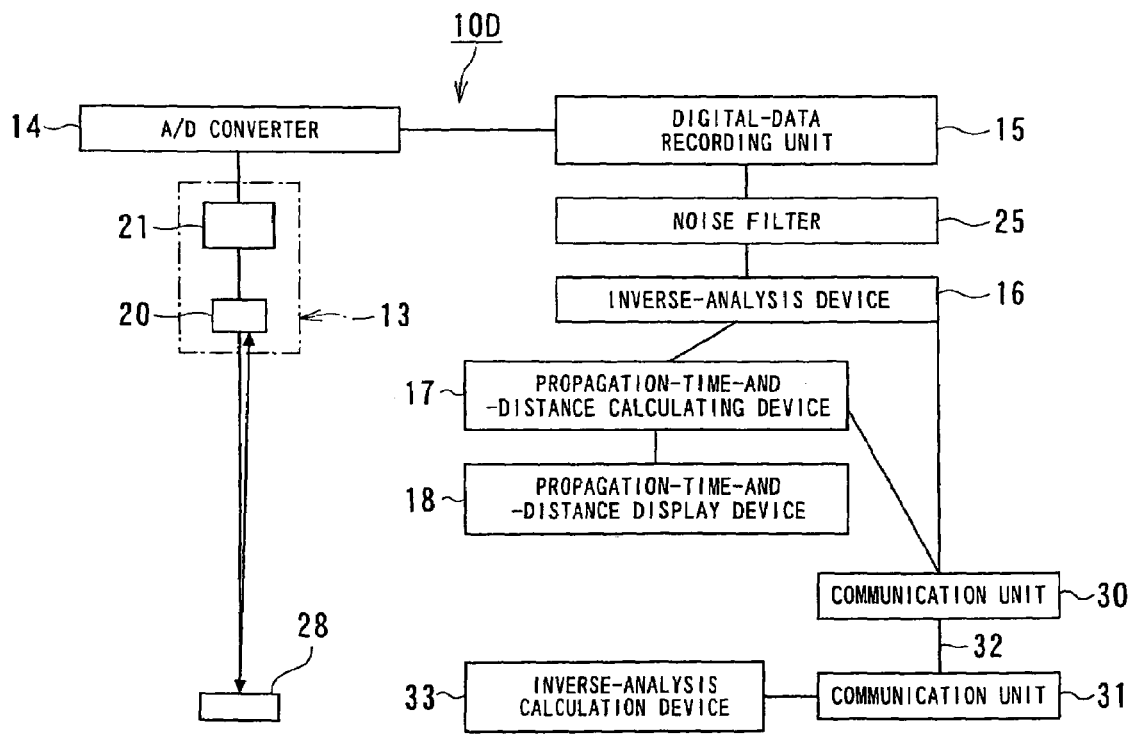
FIG. 8 is an outline block diagram showing an acoustic-propagation-time measuring apparatus according to a fifth embodiment of the present invention.

FIG. 8 shows an acoustic-propagation-time measuring apparatus according to the fifth embodiment of the present invention.

An acoustic-propagation-time measuring apparatus 10D of this fifth embodiment has basically the same structure as that of the third embodiment shown in FIG. 6, except that the acoustic-propagation-time measuring apparatus 10D additionally includes a transmitting and receiving communication unit 30, a remote communication unit 31, a communication line 32, and an inverse-analysis calculating device 33. This communication unit 30 is connected to the remote communication unit 31 via the communication line 32, such as Internet, or wirelessly to allow the inverse-analysis calculating device 33 to share the inverse analysis at the remote site. The same components as those of the acoustic-propagation-time measuring apparatus 10B shown in FIG. 6 are denoted by the same reference numerals and will not be described.

This acoustic-propagation-time measuring apparatus 10D includes the communication unit 30 in addition to the inverse-analysis device 16 and the propagation-time-and-distance calculating device 17. This communication unit 30 is connected to the communication unit 31 of the inverse-analysis calculating device 33 via, for example, the communication line 32 so that data can be transmitted and received. Using the inverse-analysis calculating device 33, such as a host computer, installed at a remote site, the acoustic-propagation-time measuring apparatus 10D adjusts matrix elements for the inverse analysis by the inverse-analysis device 16 in response to an acoustic signal reflected from the reference object 28 as a standard for calibration to produce an optimal result of the inverse analysis and carries out the inverse analysis requiring a large amount of calculation.

The inverse-analysis means 16 of the acoustic-propagation-time measuring apparatus 10D needs to carry out a huge amount of the calculation because of the huge amount of the inverse matrix calculation required for the inverse analysis. This inverse-analysis device 16 enables the inverse-analysis calculating device 33 to share the load of the calculation, thus greatly lightening the load of the calculation in the inverse-analysis device 16.

In the acoustic-propagation-time measuring apparatus 10D shown in FIG. 8, the inverse-analysis calculating device 33, based on an acoustic signal reflected from the reference object 28 as a standard for calibration, adjusts the matrix elements for the inverse analysis by the inverse-analysis device 16 to produce an optimal result of the inverse analysis and carries out the inverse analysis requiring a large amount of calculation. The inverse-analysis calculating device 33 is connected for communication to the inverse-analysis device 16 via an Internet, functioning as the communication line 32, to transmit the calculation result of the inverse analysis by the inverse-analysis calculating device 33 to the display device 18 via the propagation-time-and-distance calculating device 17. As a result, the calculation load on the inverse-analysis device 16, which requires a high calculation load, can be greatly reduced. Using the inverse-analysis calculating device 33 installed at a remote site, the acoustic-propagation-time measuring apparatus 10D can be realized by a low-cost distance-measuring apparatus.

Furthermore, a plurality of acoustic-propagation-time measuring apparatuses 10D can be connected for communication to the inverse-analysis calculating device 33 via the Internet so that the signal data can be transmitted therebetween. This enables the inverse-analysis calculating device 33 realized by a computer to be shared among the plurality of acoustic-propagation-time measuring apparatuses 10D. In short, the inverse-analysis calculating device 33 can be utilized more efficiently as a computing resource.

Figure 9:
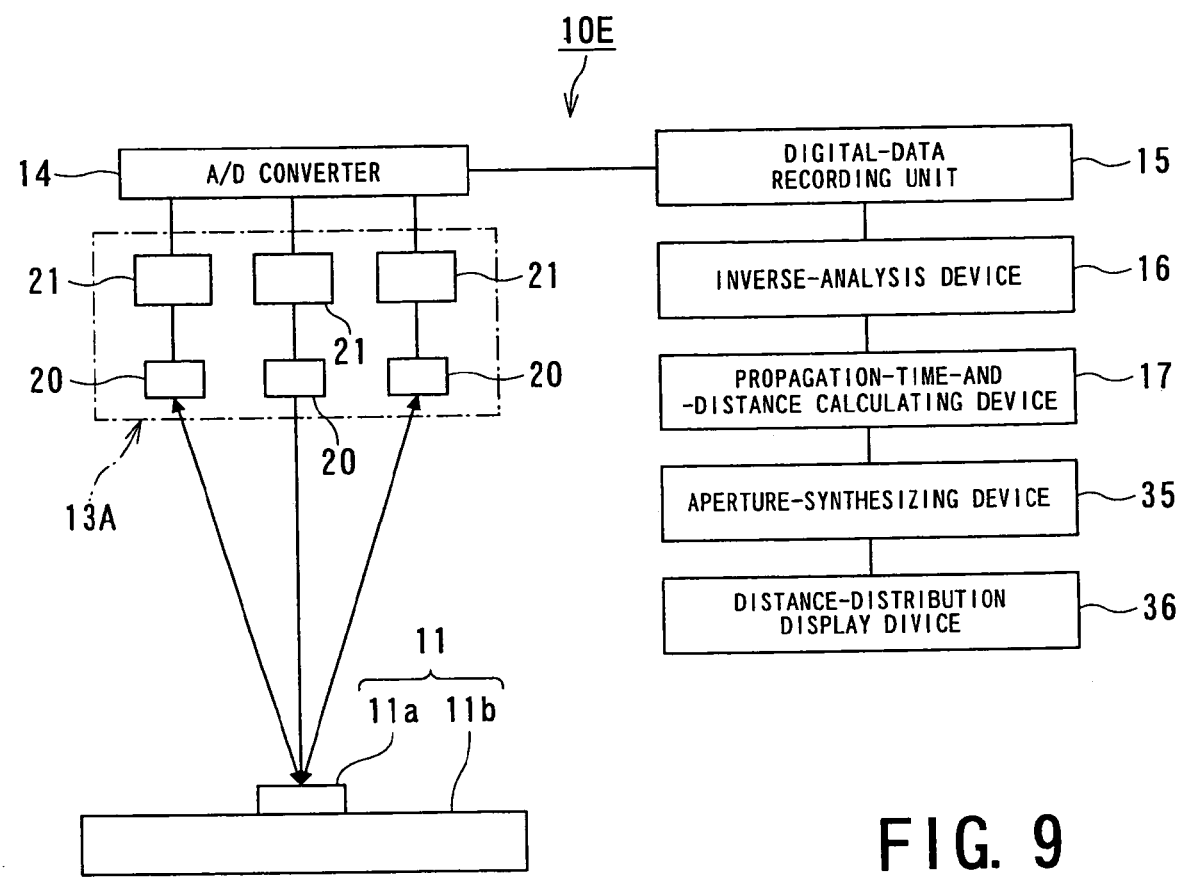
FIG. 9 is an outline block diagram showing an acoustic-propagation-time measuring apparatus according to a sixth embodiment of the present invention.
Figure 10:
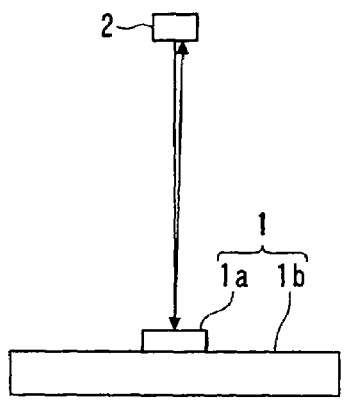
FIG. 10 illustrates the mechanism or principle of how acoustic waves are emitted from an acoustic element in a known acoustic-propagation-time measuring apparatus.
Figure 11A:
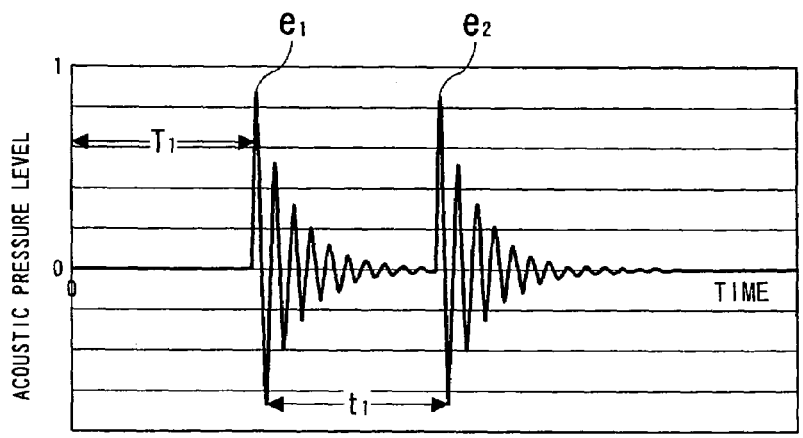
FIGS. 11A and 11B show the waveforms of acoustic receiving signals reflected from a target object as measured by a known acoustic-propagation-time measuring apparatus.
Figure 11B:
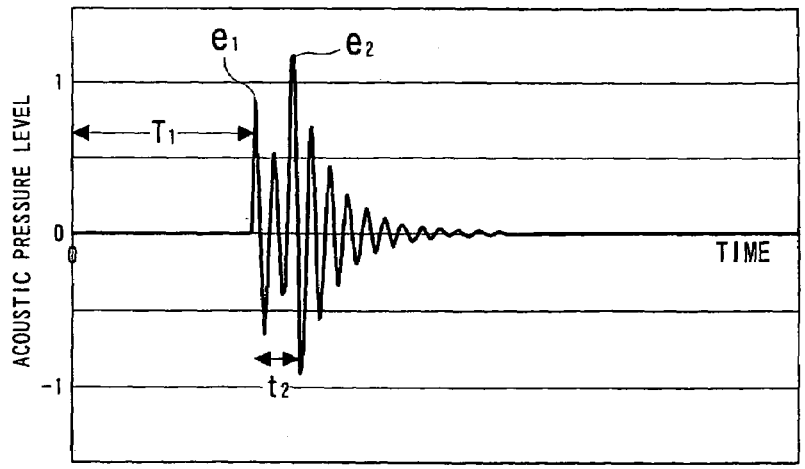

FIG. 9 shows an acoustic-propagation-time measuring apparatus according to the sixth embodiment of the present invention.

An acoustic-propagation-time measuring apparatus 10E according to this sixth embodiment has basically the same structure as that of the second embodiment shown in FIG. 5, except that the acoustic-propagation-time measuring apparatus 10E includes an aperture-synthesizing device 35 and a distance-distribution display device 36 in place of the propagation-time-and-distance display device 18 in the acoustic-propagation-time measuring apparatus 10A of the second embodiment. The same components as those of the acoustic-propagation-time measuring apparatus 10A are denoted by the same reference numerals and will not be described.

The aperture-synthesizing means 35 has small sensors arranged in line or in a matrix so as to form an integrated large sensor for the aperture synthesis or to form a synthetic aperture. With this synthetic aperture, the aperture-synthesizing device 35 carries out the calculation for imaging a measurement surface of the target object 11. With the aperture-synthesizing device 35, a bump or irregularity on the target object 11 can be measured three-dimensionally, and this three-dimensional external appearance of the target object 11 can then be displayed by the distance-distribution display device 36.

The aperture-synthesizing device 35 will operate in the following manner.

First, the aperture-synthesizing device 35 acts to switch the acoustic elements 20 for transmitting and receiving an acoustic wave signal, forms a spheroid of revolution with the foci set at the location of the acoustic element 20 which has transmitted the acoustic signal and the location of the acoustic element 20 which has received the acoustic signal, and draws the same number of such spheroids as the combinations of transmitting and receiving acoustic elements 20. Thus, the calculation for three-dimensional imaging of the measurement surface of the target object 11 is carried out to recognize the location and three-dimensional appearance of the target object 11 with high accuracy. That is, in short, the distance measurement with a wide measurable range is achieved, so that the measurement portion of the target object 11 can be recognized and measured as a three-dimensional entity.

In the foregoing embodiments according to the present invention, the inverse-analysis device 16 stores the time-series data of a reflected acoustic signal in the vertical components (column vector) of the matrix A such that the terms of the column vector (column matrix) Y, i.e., the time-series vector of the observed reflected acoustic signal yi (digital echo signal) are set as the elements $a_{kl}$ of the matrix A in which the elements $a_{kl}$ are assigned the maximum value of the acoustic pressure value in the time step of $i_{max}$. The elements $a_{kl}$ of the matrix A may be assigned the second highest peak value, instead of the maximum value of the acoustic pressure level, to produce the inverse matrix $A^{-1}$ based on the matrix A generated in this manner.

Further, it is to be noted that the present invention is not limited to the described embodiments and many other changes and modifications may be made without departing from the scopes of the appended claims.

What is claimed is:

1. An acoustic-propagation-time measuring apparatus comprising:
   an acoustic receiving device having at least one acoustic element capable of receiving a transmitted acoustic wave;
   an A/D converter for converting an acoustic receiving signal to a digital echo signal, the acoustic receiving signal being reflected from a target object to be measured and received by the acoustic element of the acoustic receiving device;
   an inverse-analysis device for carrying out inverse-analysis processing of multiplying the digital echo signal by an inverse matrix to convert the digital echo signal into an impulse signal;
   a calculating device for calculating an acoustic propagation time and a time difference of the acoustic receiving signal in response to the impulse signal produced by the inverse-analysis device; and
   a display device for displaying the acoustic propagation time and the time difference calculated by the calculating device.

2. The acoustic-propagation-time measuring apparatus according to claim 1, wherein the inverse-analysis device samples an acoustic receiving signal including an acoustic signal from the acoustic element, a characteristic of a propagation field of the acoustic signal, and a receiving characteristic of the acoustic element into vertical elements of a matrix to convert the acoustic receiving signal into time-series data in steps, produces an inverse matrix from the matrix of the time series data, and multiplies the acoustic receiving signal by the inverse matrix to convert the acoustic receiving signal into the impulse signal.

3. The acoustic-propagation-time measuring apparatus according to claim 1, wherein the inverse-analysis device adds white noise with a value being small enough compared with the acoustic receiving signal to vertical elements of a matrix containing time-series data of the acoustic receiving signal to calculate an inverse matrix, carries out the inverse-analysis processing of multiplying the acoustic receiving signal by the inverse matrix two or more times to average the results of the inverse analysis processing to calculate the mean value, and sets the mean value as the impulse signal of the acoustic receiving signal, and the calculating device calculates the acoustic propagation time and the time difference of the acoustic receiving signal.

4. The acoustic-propagation-time measuring apparatus according to claim 1, further comprising a digital data-recording unit between the A/D converter and the inverse-analysis device, the digital-data recording unit temporarily storing the digital echo signal generated by the A/D converter.

5. The acoustic-propagation-time measuring apparatus according to claim 1, wherein the acoustic receiving device includes a plurality of at least one of the acoustic elements, in which an emitting and receiving unit applies an impulse voltage to the plurality of acoustic elements.

6. The acoustic-propagation-time measuring apparatus according to claim 1, wherein the calculating device is provided with a propagation-time-and-distance calculating function for multiplying the calculated acoustic propagation time and the time difference by an acoustic velocity to measure the distance from the acoustic element to the target object, a distance difference, and bump distribution.

7. The acoustic-propagation-time measuring apparatus according to claim 1, wherein the display device is provided with a propagation-time-and-distance display function for displaying the acoustic propagation time, the time difference, the distance from the acoustic element to the target object, a distance difference, and bump distribution calculated by the calculating device.

8. The acoustic-propagation-time measuring apparatus according to claim 1, further comprising a noise filter for eliminating noise adjacent to a digital echo signal input end of the inverse-analysis device.

9. The acoustic-propagation-time measuring apparatus according to claim 1, wherein the inverse-analysis device includes inverse-analysis correcting unit for correcting an inverse-analysis result, in which the inverse-analysis correcting unit optimizes vertical elements of a matrix for the inverse-analysis processing in response to an acoustic receiving signal from a reference target object for measuring a reference acoustic propagation time.

10. The acoustic-propagation-time measuring apparatus according to claim 1, wherein the inverse-analysis device includes a communication unit connected to another remote inverse-analysis device, in which the remote inverse-analysis device receives signal data of the acoustic receiving signal from the communication unit to share the time-consuming inverse-analysis processing, transmits a result of the inverse-analysis processing to the calculating device, and the display device displays the result.

11. The acoustic-propagation-time measuring apparatus according to claim 1, wherein the calculating device includes aperture-synthesizing unit for carrying out calculation of imaging a measurement surface of the target object by aperture synthesis, the measurement surface being subjected to three-dimensional measurement.

* * * * *